United States Patent [19]

Kaiser

[11] 4,225,501

[45] Sep. 30, 1980

[54] 1,4-EPOXY-1,3,3-TRIMETHYL-2-(2-BUTEN-1-YLIDENE)-CYCLOHEXANES

[75] Inventor: Roman Kaiser, Uster, Switzerland

[73] Assignee: Givaudan Corporation, Clifton, N.J.

[21] Appl. No.: 924,030

[22] Filed: Jul. 12, 1978

[30] Foreign Application Priority Data

Jul. 25, 1977 [LU] Luxembourg ............................ 77834
May 19, 1978 [CH] Switzerland .......................... 5464/78

[51] Int. Cl.$^3$ ............................................ C07D 307/28
[52] U.S. Cl. ............................ 260/346.22; 252/522 R; 426/536; 426/583; 426/597; 426/599; 560/259; 568/823
[58] Field of Search .................................. 260/346.22

[56] References Cited

PUBLICATIONS

Arctander, Perfume & Flavor Materials of Natural Origin, (1960), p. 500.

Kaiser et al., Helvetica Chimica Acta, vol. 61, No. 1, (1978), pp. 373–382.
Yamada et al., J.C.S. Chem. Comm., 1976, pp. 997–998.
Goldsmith, J.A.C.S., vol. 84, (1962), pp. 3913–3914.
Caglioti et al., Helvetica Chimica Acta., vol. 42, No. 7, (1959), pp. 2557–2570.

*Primary Examiner*—Henry R. Jiles
*Assistant Examiner*—Bernard Dentz
*Attorney, Agent, or Firm*—Robert F. Tavares; Thomas Cifelli, Jr.

[57] ABSTRACT

The invention is concerned with odorant and/or flavoring substances, a process for the manufacture thereof, odorant and/or flavoring compositions containing same and a process for the preparation of said compositions. The invention is also concerned with a method of imparting an odor and/or a flavor to materials using said substances or compositions.

4 Claims, No Drawings

1,4-EPOXY-1,3,3-TRIMETHYL-2-(2-BUTEN-1-YLIDENE)-CYCLOHEXANES

The odorant and/or flavoring substances provided by the present invention are compounds of the general formula

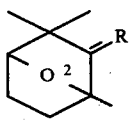

I wherein R represent the 2-cis-or the 2-trans-buten-1-ylidene group.

FIELD OF THE INVENTION

This invention relates to the field of fragrances and flavorants.

SUMMARY OF THE INVENTION

"ODORANT AND/OR FLAVOURING SUBSTANCES"

The present invention relates to odorant and/or flavouring substances. More particularly, the invention is concerned with odorant and/or flavouring substances, a process for the manufacture thereof, odorant and/or flavouring compositions containing same and a process for the preparation of said compositions. The invention is also concerned with a method of imparting an odour and/or a flavour to materials using said substances or compositions.

The odorant and/or flavouring substances provided by the present invention are compounds of the general formula

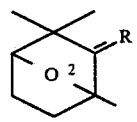

I wherein R represents the 2-cis- or the 2-trans-buten-1-ylidene group.

The foregoing formula accordingly embraces the compounds of the formulae

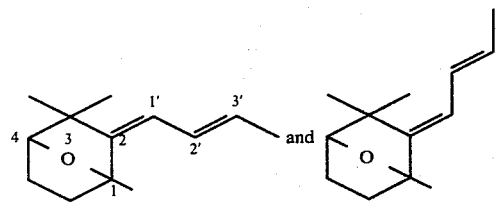

Ia
cis/trans

Ib
trans/trans

-1,4-epoxy-1,3,3-trimethyl-2-(2-buten-1-ylidene)-cyclohexane.

Moreover, the formulae are intended to embrace each of the two possible geometric isomers having regard to the cis/trans isomerism (2'-position) present.

DESCRIPTION OF THE PREFERRED EMBODIMENTS

According to the process provided by the present invention, the compounds of formula I hereinbefore are manufactured by heating 1,3,3-trimethyl-2-(3-hydroxybutylidene)-6-cyclohexen-4-ol in acid medium.

The acid medium can be provided by means of mineral acids such as sulphuric acid or hydrochloric acid, acid salts such as bisulphates (e.g. potassium bisulphate) or acid earths such as diatomaceous earths (e.g. Filtrol). However, suitable organic acids such as those acids which are moderately strong to strong can also be used. Examples of such organic acids are alkanesulphonic acids (e.g. methanesulphonic acid), p-toluenesulphonic acid and picric acid.

The temperature at which the heating is carried out is not critical. It conveniently amounts to ca 20°–200° C., preferably 60°–130° C. The heating is conveniently carried out at higher temperatures when a weak acid is used and at lower temperatures when a strong acid is used.

The heating is preferably carried out in the presence of an organic solvent, especially an aromatic solvent. Examples of such solvents are benzene, toluene, xylene etc.

According to the process provided by the present invention there is obtained a mixture of compounds of formulae Ia and Ib in the approximate ratio of 15:85. Traces of the cis/cis and the trans/trans isomers can be detected in the mixture. The isomer mixture can be separated in the usual manner; for example, by column chromatography or preparative gas chromatography. As will be evident from the following, the isomers do not differ fundamentally in their organoleptic properties, so that on economical grounds the isomer mixture can be used.

The 1,3,3-trimethyl-2-(3-hydroxybutylidene)-6-cyclohexen-4-ol, referred to hereinafter as compound 14, is a novel compound and also forms part of the invention. It can be obtained from the known 2-hydroxy-β-ionone.

For this purpose, this 2-hydroxy-β-ionone is conveniently reacted with an enol acylate in the presence of one of the aforementioned acids; for example dissolved in (an excess of) acetone enol acetate, the solution is treated with a catalytic amount of p-toluenesulphonic acid and the mixture is held at reflux temperature for 1–2 hours. The diacetate 13 obtained after working-up can be converted directly into the diol 14 by treatment with a strong reducing agent such as lithium aluminium hydride.

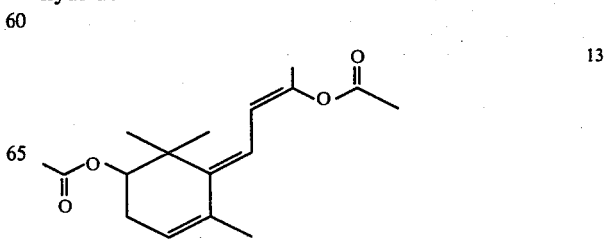

13

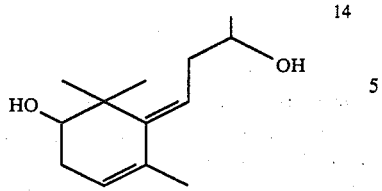

The diacetate 13 is novel and also forms part of the present invention.

The compounds of formula I have particular organoleptic properties, on the basis of which they are excellently suited as odorant and/or flavouring substances.

The invention is therefore also concerned with a method of imparting an odour and/or a flavour to materials, which method comprises applying to said materials or incorporating therein a compound of formula I, especially in practically pure form or in the form of mixtures (with the exception of natural mixtures containing a compound of formula I) or of an odorant and/or flavouring composition containing same.

The expression "practically pure" is used herein to mean, in particular, a compound of formula I which is free from accompanying substances which are present besides compounds of formula I in natural extracts. As practically pure compounds of formula I in the scope of the present invention there should be understood, in particular, synthetically manufactured compounds of formula I.

The natural mixtures containing compounds of formula I should thus be excluded, since in the course of the present investigations it has been found that compounds of formulae Ia and Ib in the ratio of 1:5 are contained in osmanthus absolute.

The compounds of formula I, especially the compound of formula Ib because of its greater diffusion and intensity, are characterised by fresh, green, spicy, very natural olfactory nuances reminiscent in certain respects of cassis buds and exotic fruits such as mango, passion fruit and guanabana. The compounds of formula I can therefore be used for the perfuming or flavouring of products such as cosmetics (soaps, ointments, powders, toothpastes, mouth washes, deodorants, shampoos, lotions etc), detergents or foodstuffs, luxury consumables and drinks, the compounds preferably not being used alone but rather in the form of compositions which contain other odorant or flavouring substances. Such odorant or flavouring compositions containing a compound of formula I and the preparation of such compositions in a manner known per se (addition of a compound of formula I to known odorant or flavouring compositions or admixture of a compound of formula I with natural or synthetic compounds or mixtures suitable as components of odorant or flavouring compositions) also form part of the present invention.

On the basis of their aforementioned original notes, the compounds of formula I, especially the compound of formula Ib, are suitable as odorant substances, especially in combination with a series of natural and synthetic odorant substances such as, for example:

Galbanum oil, mastix oil, vetiver oil, patchouli oil, sandalwood oil, mandarin oil, petitgrain oil, ylang-ylang oil, basil oil, tree moss absolute, patchouli leaf oil, cedar oil, spruce oil, laurel oil, costusroot oil, calamus oil, mugwort oil, camomile oil, wormwood oil, wormseed oil, celery seed oil, angelica seed oil, star anis oil, thyme oil, rosemary oil, lavender oil, lavandin oil, aspic oil, sage oil, neroli oil, bergamotte oil, lemon oil, orange oil, grapefruit oil, geranium oil, benzoin resinoid, melilotus absolute, jasmin absolute, rose oil, cananga oil, coriander oil, cassia absolute, narcissus absolute, verbena absolute or oil, violet leaf absolute, tuberose absolute etc;

aldehydes such as hydroxycitronellal, cyclamen aldehyde, p-tert.butyl-α-methylhydrocinnamaldehyde, α-hexylcinnamaldehyde, 3,5-dimethyl-cyclohex-3-en-1-yl-carboxaldehyde, citral, citronellal, 2,6-dimethyl-6-hepten-1-al, isovaleraldehyde, trans-2-hexenal, sorbic aldehyde, trans-2-octenal, n-octanal, n-nonanal, trans-2,cis-6-nonadienal, 2,4-decadienal, methylnonylacetaldehyde etc;

ketones such as α-ionone, β-ionone, allylionone, acetanisole, 4-(p-hydroxyphenyl)-2-butanone, camphor, menthone, carvone, pulegone etc;

acetals and ketals such as phenylacetaldehyde dimethylacetal, phenylacetaldehyde glycerinacetal, 2-methyl-1,3-dioxolan-2-ethyl acetate, capronaldehyde dimethylacetal etc;

ethers such as eugenol methyl ether, methyl 1-methylcyclododecyl ether, anethol, estragol etc;

phenolic compounds such as eugenol, isoeugenol, creosol etc;

alcohols such as butanol, cis-3-hexanol, trans-2,cis-6-nonadienol, cis-6-noneol, linalool, geraniol, nerol, citronellol, nerolidol, farnesol, benzyl alcohol, phenylethyl alcohol, cinnamic alcohol etc;

esters such as methyl dihydrojasmonate, linalyl acetate, geranyl acetate, cedryl acetate, vetiveryl acetate, ethyl isovalerate, ethyl caproate, p-tert.butylcyclohexyl acetate, o-tert.butylcyclohexyl acetate, myraldyl acetate (Trade Mark) (Givaudan), benzyl acetate, benzyl salicylate, styrallyl acetate, ethyl α-methylphenylglycidate, ethyl trans-2-hexenoate, ethyl trans-2-octenoate etc;

lactones such as γ-undecalactone, γ-decalactone, γ-nonalactone, δ-decalactone, δ-octalactone, coumarin etc;

acids such as lactic acid, butyric acid, α-methylbutyric acid, trans-2-hexenoic acid, trans-2-octenoic acid etc;

compounds having a musk-like and amber-like odour such as ethylene brassylate, 4-acetyl-6-tert.butyl-1,1-dimethylindane, 12-oxahexadecanolide, 8α,12-oxido-13,14,15,16-tetranorlabdane etc;

sulphur-containing compounds such as p-menthane-8-thiol-3-one, dimethylsulphide and other sulphides and disulphides etc; and nitrogen-containing compounds such as methyl anthranilate, indole, isobutylquinoline, various pyrazines, 5-methyl-heptan-3-onoxime etc.

The odorant compositions prepared using compounds of formula I, especially odorant compositions of the chypre, cologne or muguet type or odorant compositions having a general flowery and woody direction, are especially attractive by their impressive freshness and originality.

In the preparation of such odorant compositions, the aforementioned known odorant substances can be used in a manner which is known to the perfumer; for example, as described by W. A. Poucher, Perfumes, Cosmetics and Soaps 2, 7th edition, published by Chapman and Hall, London, 1974.

Finally, it has been shown that the compounds of formulae Ia and Ib can also be used in the reconstitution of a series of essential oils or absolutes (e.g. mandarin oil, grapefruit oil, cassis-bud absolute) in which these compounds have never been detected.

The concentration of the compounds of formula I can vary within wide limits depending on the purpose of use; for example, between about 0.01 wt.% in the case of detergents and about 15 wt.% in the case of alcoholic solutions. In perfume bases or concentrates the concentrations can, of course, also be higher. The perfume bases can be used in the usual manner for the perfuming of Eau de Cologne, eau de toilette, lotions, creams, shampoos, soaps, detergents etc.

As flavouring substances, the compounds of formula I can be used, for example, for the production or improvement, intensification, enhancement or modification of fruit or berry aromas in foodstuffs (yoghurt, sweet goods etc), in luxury consumables (tea etc) and drinks (lemonades etc).

The pronounced flavour qualities of especially practically pure, and especially of synthetically manufactured, compounds of formula I enable them to be used in low concentrations. A suitable range is, for example, 0.1 ppm–100 ppm, preferably 1 ppm–20 ppm, in the finished product (i.e. the flavoured foodstuff, luxury consumable or drink).

Some effects which can be achieved with the compounds of formula I are compiled in the following Table.

Table

| Flavour | Concentration | Effect |
| --- | --- | --- |
| Passion fruit | ppm in the finished product 0.1–30 ppm especially 0.5–4 ppm | Greater naturalness of the fruit character, complete flavour |
| Grapefruit | ppm in the finished product 0.1–100 ppm especially 1–20 ppm | Very natural fruit character |
| Mango | ppm in the finished product 0.1–50 ppm especially 0.5–10 ppm | Reinforces the character of the fresh, ripe mango fruit |

The compounds of formula I can be mixed with the components used for flavouring compositions or added to such flavourants in the usual manner. Among the flavourants contemplated in accordance with the present invention there are to be understood flavouring compositions which can be diluted or dispersed in edible materials in a manner known per se. They can be converted according to methods known per se into the usual forms of use such as solutions, pastes or powders. The products can be spray-dried, vacuum-dried or lyophilised.

The known flavouring substances which are conveniently used in the preparation of such flavourants are either referred to hereinbefore or can readily be obtained from the literature such as, for example, J. Merory, Food Flavorings, Composition, Manufacture and Use, Second Edition, The Avi Publishing Company, Inc., Westport, Conn. 1968, or G. Fenaroli, Fenaroli's Handbook of Flavor Ingredients, Second Edition, Volume 2, CRC Press, Inc., Cleveland, Ohio, 1975.

For the preparation of such usual forms of use there come into consideration, for example, the following carrier materials, thickening agents, flavour-improvers, spices, auxiliary ingredients etc:

Gum arabic, tragacanth, salts or brewer's yeast, alginates, carrageen or similar absorbents; indoles, maltol, spice oleoresins, smoke flavours; cloves, sodium citrate; monosodium glutamate, disodium inosine-5'-monophosphate (IMP), disodium guanosine-5-phosphate (GMP); or special flavouring substances, water, ethanol, propyleneglycol, glycerine.

The following Example illustrates the preparation of the compounds of formula I:

EXAMPLE 1

A solution of 25.0 g (0.129 mol) of α-saffron acid ethyl ester 2 and 0.25 g of rose bengal in 300 ml of ethanol was exposed to light for 2 hours in a Pyrex glass exposure apparatus while simultaneously bubbling pure oxygen through the solution. A centrally-arranged water-cooled mercury high-pressure emitter (Hanau type TQ-150) was used as the light source. The average oxygen uptake amounted to about 30 ml/minute. The course of the reaction was followed by chromatography (decrease of the educt).

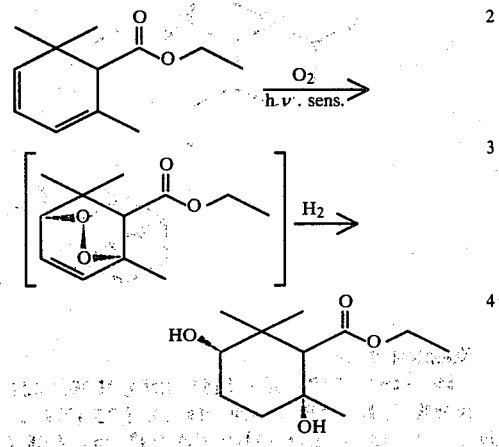

The thus-obtained ethanolic solution of the 1,4-epidioxy-1,3,3-trimethyl-2-ethoxycarbonyl-5-cyclohexene 3 was treated with 0.3 g of platinum (IV) oxide and subsequently hydrogenated at normal pressure up to saturation. The hydrogen consumption amounted to 4.95 liters in 1.5 hours ( 77.5% of theory). The solution was freed from catalyst by filtration, concentrated and the resulting 31 g of crude product was chromatographed on a 20-fold amount of silicagel. Elution with ether gave 14.0 g of cis-2,5-dihydroxy-2,6,6-trimethylcyclohexane carboxylic acid ethyl ester 4 of melting point 92°–94° C. (yield = 51%, purity greater than 98%).

Spectral data:

IR: 3600, 3450, 1720, 1333, 1142, 1031, 1025, 932, 891 $cm^{-1}$ (as a solution in chloroform);

NMR: 1.02 + 1.18 (each 3H, s); 1.23 (3H, s); 1.28 (3H, t, J ~ 6.8 Hz); 2.57 (1H, s); 3.90 (1H, m, $J_{ax-ax}$ ~ 8 Hz, $J_{ax-eq}$ ~ 4 Hz); 4.15 (2H, q, J ~ 6.8 Hz); δ ppm;

MS: 212 (M+ − H₂O, 13), 166 (34), 154 (15), 129 (100), 123 (25), 113 (15), 101 (68), 95 (24), 83 (43), 43 (90).

34.9 g (0.152 mol) of the dihydroxy ester 4 and 3.0 g of p-toluenesulphonic acid were dissolved in 250 ml of toluene and subsequently stirred at the reflux temperature of the mixture for 2 hours while simultaneously removing the water formed. The cooled solution was diluted with 200 ml of ether, washed three times with soda solution and three times with water, dried over sodium sulphate and concentrated. There were obtained 32.0 g of crude product which, according to gas chromatographical analysis, contained 83% or 10%, respectively, of the 2-hydroxy-α- and β-cyclogeranium acid ester 5 and 6. The 2,5-oxaester 7 was obtained as the byproduct in an amount of 7%.

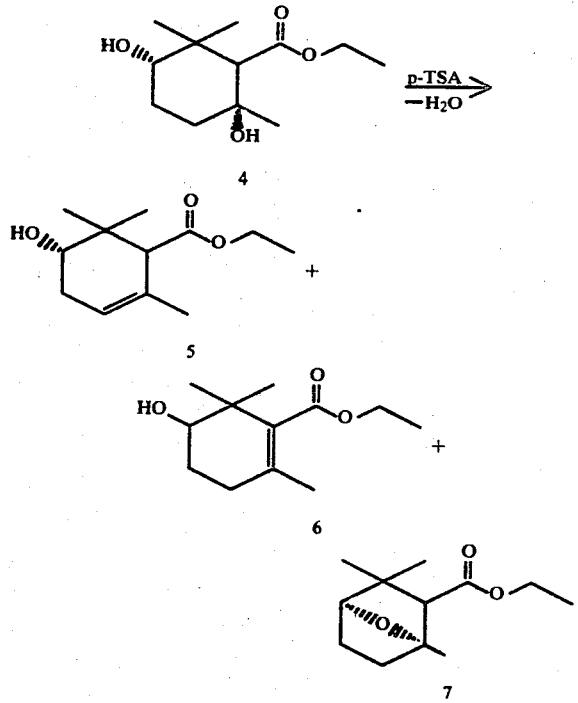

Spectral data:

5 IR: 3460, 1730, 1336, 1151, 1049, 1039, 1029 cm⁻¹;

NMR: 0.92+0.98 (each 3H, s); 1.25 (3H, t, J~6.8 Hz); 1.62 (3H); 2.76 (1H); 4.0 (1H, m); 4.08 (2H, q, J~6.8 Hz); 5.4 (m, 1H) δ ppm;

MS: 212 (M+, 9); 194 (25), 166 (28), 141 (19), 139 (27), 123 (28), 121 (100), 113 (32), 107 (18), 95 (53), 43 (27);

6 IR: 3460, 1720, 1280, 1235, 1030 cm⁻¹;

NMR: 1.12 (6H, 2s); 1.30 (3H, t, J~6.8 Hz); 1.67 (3H, s); 3.52 (1H, m); 4.20 (2H, q, J~6.8 Hz) δ ppm;

MS: 212 (M+, 6); 169 (69), 139 (55), 125 (42), 123 (81), 121 (42), 96 (63), 95 (68), 79 (40), 67 (35), 55 (43), 43 (100);

7 IR: 1730, 1310, 1216, 1179, 1119, 1046, 1000, 871 cm⁻¹;

NMR: 0.98+1.21 (6H, 2s); 1.24 (3H, t, J~6.8 Hz); 1.45 (3H, s); 2.29 (1H); 3.90 (1H, d, J~4 Hz); 4.11 (2H, q, J~6.8 Hz) δ ppm;

MS: 212 (M+, 15), 197 (45), 167 (64), 154 (76), 139 (50), 130 (84), 121 (65), 109 (36), 95 (52), 83 (44), 55 (39), 43 (100).

The foregoing crude product (32.0 g) dissolved in 80 ml of tetrahydrofuran was allowed to drop over a period of 30 minutes into a suspension of 4.60 g (0.12 mol) of lithium aluminium hydride in 300 ml of anhydrous tetrahydrofuran. The resulting mixture was stirred at reflux for 16 hours. The mixture, cooled to 0° C., was cautiously treated with water and then with 2-N hydrochloric acid solution and subsequently taken up in 400 ml of ether. The ethereal layer was washed with water, dried and concentrated. There were obtained 26.2 g of crude product which, according to gas chromatographical analysis, contained 80% of 2-hydroxy-α-cyclogeraniol 8.

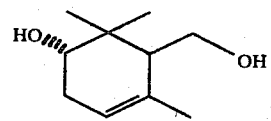

A sample recrystallised from ether showed the following spectroscopic data:

IR: 3615, 3450, 1175, 1068, 1037, 1018, 955, 845 cm⁻¹ (as a solution in chloroform);

NMR: 0.90+1.09 (each 3H, 2s); 1.75 (3H); 3.80 (2H, d, J~4 Hz); 3.95 (1H, m); 5.50 (1H, m) δ ppm;

MS: 170 (M+, 1), 152 (83), 121 (80), 109 (36), 107 (52), 95 (47), 93 (34), 81 (79), 72 (59), 55 (42), 43 (100), 41 (51):

Melting point: 103°-104° C.

15.0 g (0.088 mol) of crude 2-hydroxy-α-cyclogeraniol 8 were dissolved in 60 ml of methyl chloride and added dropwise over a period of 10 minutes to a solution of 19.0 g (0.088 mol) of pyridinium chlorochromate [E. J. Corey, J. W. Suggs, Tet. Lett. 31, 2647 (1975)] in 250 ml of methyl chloride so that the temperature remained between 20° C. and 25° C. Subsequently, the mixture was stirred at room temperature for a further 20 minutes, the solution was decanted off from the precipitate formed, the precipitate was rinsed twice with methylene chloride and the combined organic phases were washed with water, 2-N hydrochloric acid, bicarbonate solution and again with water. After drying and concentration, there were obtained 11.9 g of crude product which contained the two hydroxyaldehydes

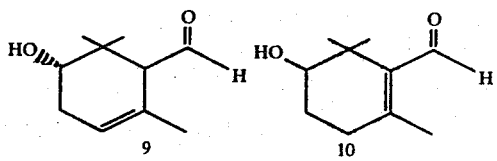

in the ratio of 3:1.

Spectral data:

9 MS: 168 (M+, 23), 150 (14), 137 (38), 121 (55), 107 (42), 97 (59), 95 (44), 79 (28), 72 (30), 55 (40), 43 (10);

10 MS: 168 (M+, 16), 137 (100), 123 (15), 109 (31), 95 (11), 81 (46), 79 (14), 70 (78), 67 (31), 55 (13), 41 (21).

11.9 g of the crude aldehyde mixture 9/10 were dissolved in 120 ml of acetone, treated with 23 ml of 10% aqueous potassium hydroxide solution and subsequently stirred at reflux for 19 hours. Half of the acetone was distilled off under reduced pressure, the concentrate was taken up in 200 ml of ether and the ethereal solution was washed with concentrated sodium chloride solution. After drying and concentration, there were obtained 12.5 g of crude product which, according to gas chromatographical analysis, consisted of about 40% of the 2-hydroxy-β-ionones 11 and 12 in the ratio of 1:5. Purification of the crude product by column chromatography yielded, upon elution with hexane-ether (1:1), 4.2 g of a 92% mixture of the 2-hydroxy-ionones 11 and 12.

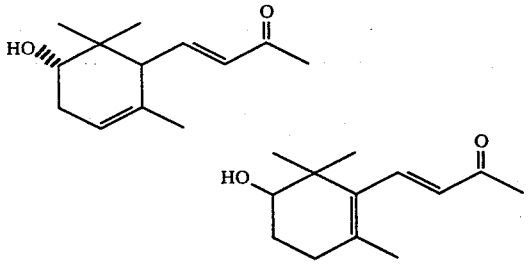

For the spectroscopic characterisation there were used samples which had been brought to a purity of greater than 95% by preparative gas chromatography.

Spectral data:

11 IR: 3450, 1670, 1620, 1256, 1051, 989, 905, 815 cm$^{-1}$;

NMR: 0.96 (6H, 2s); 1.58 (3H); 2.27 (3H, s); 2.54 (1H, d, J~10 Hz); 3.68 (1H, dxd, $J_{ax-ax}$~7 Hz, $J_{ax-eq}$~5 Hz); 5.44 (1H, m); 6.08 (1H, d, J~16 Hz); 6.68 (1H, dxd, $J_1$~16 Hz), $J_2$~10 Hz) δ ppm;

MS: 208 (M+, 1); 175 (51), 157 (10), 147 (19), 137 (26), 121 (43), 109 (13), 93 (51), 77 (14), 72 (21), 43 (100);

12 IR: 3460, 1665, 1608, 1256, 1190, 1175, 1115, 1042, 1005 978 cm$^{-1}$;

NMR: 1.08+1.11 (each 3H, 2s); 1.75 (3H); 2.29 (3H, s); 3.56 (1H, dxd, $J_{ax-ax}$~7 Hz, $J_{ax-eq}$~4.6 Hz); 6.10 (1H, d, J~16.5 Hz); 7.21 (1H, d, J~16.5 Hz) δ ppm;

MS: 208 (M+, 2), 193 (69), 175 (44), 157 (8), 149 (26), 147 (20), 121 (36), 105 (33), 83 (16), 81 (19), 79 (14), 43 (100).

3.87 g of the 2-hydroxy-ionones 11/12 (1:5) were dissolved in 20 ml of acetone enol acetate and subsequently stirred at reflux temperature for 2 hours in the presence of 0.03 g of p-toluenesulphonic acid. The mixture was cooled, taken up in 150 ml of ether, the ethereal phase was washed with bicarbonate solution and water, dried and concentrated. There were obtained 4.5 g of 4-acetoxy-1,3,3-trimethyl-2-(3-acetoxy-2-butenylidene)-cyclohex-6-ene 13 which was further processed directly to the diol 14 as follows:

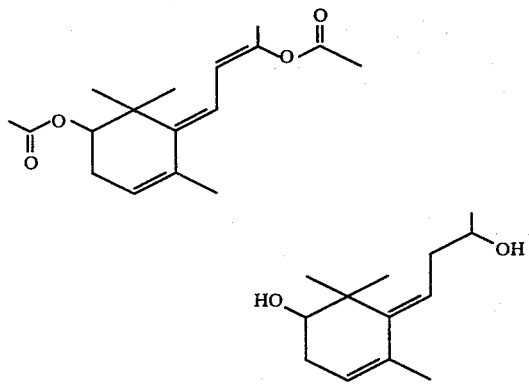

A solution of 3.9 g of diacetate 13 in 10 ml of ether was allowed to drop over a period of 10 minutes into a suspension of 1.06 g of lithium aluminium hydride in 70 ml of ether. The mixture was stirred at reflux for 1 hour, cooled to room temperature, the excess lithium aluminium hydride was cautiously decomposed with water and the ether phase was washed with water, dried and concentrated. The residual 2.7 g of diol 14 were dissolved, together with 0.05 g of p-toluenesulphonic acid, in 25 ml of benzene, the mixture was subsequently stirred at reflux temperature for 1 hour, the cooled mixture was diluted with 50 ml of ether and the ether phase was washed with bicarbonate solution and water. After drying and concentration, there were obtained 2.3 g of crude product which, according to gas chromatographical analysis, consisted of about 50% of 1,4-epoxy-1,3,3-trimethyl-2-(2-buten-1-ylidene)-cyclohexane 1a and 1b (ratio cis/trans=15:85) besides viscous compounds.

By bulb-tube distillation of the crude product there was obtained 0.95 g of product which consisted to above 92% of the isomer mixture. The mixture has a fresh, green, spicy, very naturally acting odour which is reminiscent in certain respects of tomato leaves, cassis buds and exotic fruits.

For the spectroscopic characterisation there were used samples of the individual isomers which had been brought to a purity of above 98% by chromatography on a 40-fold amount of silica gel [hexane/ether (30:1)]. Spectral data:

1a IR: 1410, 1183, 1118, 1019, 1002, 990, 961, 928, 878, 833, 770 cm$^{-1}$;

NMR: 1.04+1.13 (each 3H, s); 1.75 (3H, s); 1.78 (3H, d, J~7 Hz); 3.93 (1H, d, J~4 Hz); 5.55 (1H, dxq, $J_{3',2'}$~16 Hz, $J_{3',CH_3}$~7 Hz), ~5.55 (1H, d, J~10 Hz), ~6.3 (1H, dxd, $J_{2',3'}$~16 Hz, $J_{2',1'}$~10 Hz);

MS: 192 (M+, 24); 149 (16), 136 (22), 123 (45), 121 (35), 109 (49), 93 (26), 91 (32), 81 (44), 69 (86), 43 (100);

1b IR: 1421, 1235, 1195, 1117, 1021, 1003, 963, 872, 823 cm$^{-1}$;

NMR: 1.28 (6H, 2s); 1.50 (3H, s); 1.78 (3H, d, J~7 Hz); 3.89 (1H, d, J~4 Hz); 5.55 (1H, dxq, $J_{3',2'}$~16 Hz; $J_{3',CH_3}$~7 Hz); 5.65 (1H, d, $J_{1',2'}$~10 Hz); 6.30 (1H, dxd, $J_{2',3'}$~16 Hz; $J_{2',1'}$~10 Hz);

MS: 192 (M+, 24), 149 (12), 136 (12), 123 (39), 121 (22), 109 (36), 93 (18), 91 (18), 81 (33), 69 (82), 43 (100).

The following Examples illustrate odorant and/or flavouring compositions provided by the present invention. In these Examples, the term "compound I" means the isomer mixture obtained in Example 1.

EXAMPLE A

Green base

|  | Parts by weight |
|---|---|
| Methyl dihydrojasmonate | 400 |
| Bergamotte oil | 200 |
| Propyleneglycol | 145 |
| Allyl ionone | 50 |
| Fixateur 404 (Trade Mark) (8α, 12-oxido-13,14,15,16-tetranorlabdane) | 5 |
|  | 800 |

When there are added to this conventional green base (sage direction) 200 parts of the compound I, the base is very agreeably rounded-off in the direction of tomato leaves and cassis buds. The compound I fits very harmoniously into the complex and confers to it a fresh, woody somewhat dry and much less sweet note.

EXAMPLE B

Perfumery composition (grapefruit, lemon peel direction).

|  | Parts by weight |
| --- | --- |
| Bergamotte oil | 300 |
| Mandarin oil | 150 |
| Galbanum oil | 100 |
| Ethylene brassylate (Trade Mark) Givaudan | 50 |
| p-Methane-8-thiol-3-one | 1 |
| Solvent ad | 900 |

When 100 parts of the compound I are added to this base, which has a blackcurrant character, the cassis note disappears in favour of a very agreeable fresh note in the direction of grapefruit and lemon peel. As is evident, the compound I combines very harmoniously with sulphur-containing compounds. The novel base takes on a very natural freshness. Surprisingly, this fresh effect is still very clearly perceptible even after 24 hours.

EXAMPLE C

Perfumery composition (green note)

|  | Parts by weight |
| --- | --- |
| Linalyl acetate | 300 |
| α-Hexyl cinnamaldehyde | 300 |
| Benzyl salicylate | 300 |
| Methyl dihydrojasmonate | 30 |
| Methyl anthranilate | 10 |
| Basil oil | 10 |
| Cyclal (Trade Mark) Givaudan (3,5-dimethyl-cyclohex-3-ene-1-carboxaldehyde) (10% in propyleneglycol) | 5 |
| Galbanum oil | 5 |
|  | 960 |

When there are added to this green base 40 parts of the compound I, then the composition becomes more diffuse, fresh and natural. The green note takes on a fruity aspect in the direction of cassis buds. The complex of galbanum oil and methyl dihydrojasmonate, essential for the green note, is underlined in an extremely advantageous manner by the addition of the compound I.

EXAMPLE D

Perfumery composition (masculine chypre note)

|  | Parts by weight |
| --- | --- |
| Bergamotte oil | 300 |
| Citronellol | 160 |
| Patchouli oil | 100 |
| Vetiver oil | 100 |
| Hydroxycitronellal | 80 |
| Eugenol extra | 70 |
| Tree moss absolute | 40 |
| Geraniol | 40 |
| Methyl eugenol | 30 |
| Styrallyl acetate | 20 |
| Sandalwood oil | 20 |
| Methylnonylacetaldehyde (10% in propyleneglycol) | 10 |
| Methyl dihydrojasmonate | 8 |
| Phenylacetaldehyde dimethyl acetal | 2 |

-continued

|  | Parts by weight |
| --- | --- |
|  | 980 |

When this composition (chypre character) is treated with 20 parts of the compound I, then the final composition becomes more lively, simultaneously becomes more rounded-off and clearly has more character of a "finished" cologne. The novel composition is well suited for the production of a masculine cologne.

EXAMPLE E

Perfumery composition (muguet character)

|  | Parts by weight |
| --- | --- |
| Hydroxycitronellal | 440 |
| Rhodinol | 340 |
| Linalool | 90 |
| α-Amyl cinnamaldehyde | 50 |
| Sandalwood oil | 50 |
| Ylang-ylang oil Bourbon | 20 |
|  | 990 |

When this conventional muguet composition is treated with 10 parts of the compound I, then there is immediately established a clear improvement of the olfactory impression in the direction of the natural odour. Certain aspects of dew-fresh lilies of the valley now come into play very well.

EXAMPLE F 1 liter of a commercial passion fruit juice was treated with 0.35 g of a 0.1% alcoholic solution of 1,4-epoxy-1,3,3-trimethyl-2-(2-butenylidene)-cyclohexane. A further 1 liter of passion fruit juice was treated with 0.35 g of pure alcohol. The two fruit juices were submitted to test panel comprising 10 persons. The majority of the panel (8 persons) stated that in the additionally flavoured sample the agreeable sweet and exotic odour of the passion fruit clearly came into play better.

EXAMPLE G

In an analogous manner to that described in Example F, 1 liter of grapefruit juice was treated with 0.40 g of a 0.1% alcoholic solution of 1,4-epoxy-1,3,3-trimethyl-2-(2-butenylidene)-cyclohexane. In this case, in comparison with a blind sample, the majority of the panel (8 persons) detected in the additionally flavoured sample a pronounced woody note and, moreover, there was very positively noticed an association with ripe grapefruit fruit.

EXAMPLE H 1 kg of "natural" yoghurt was treated with 100 g of mango fruit pulp and 80 g of saccharose. To 500 g of this mango yoghurt was added 0.25 g of a 0.1% alcoholic solution of 1,4-epoxy-1,3,3-trimethyl-2-(2-butenylidene)-cyclohexane. The two yoghurts were submitted to the test panel (10 persons) and judged in comparison to a fresh mango fruit. The majority of the panel (6 persons) found in the additionally flavoured yoghurt clearly substantially more character of the fresh mango fruit.

What is claimed is:
1. Compounds of the general formula:

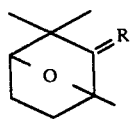

wherein R represents the 2-cis or the 2-trans-buten-1-ylidene group with the exception of natural mixtures containing compounds of formula I.

2. The compound of claim 1 having the formula: cis/trans-1,4-epoxy-1,3,3-trimethyl-2-(2-buten-1-ylidene)-cyclohexane.

3. The compound of claim 1 having the formula: trans/trans-1,4-epoxy-1,3,3-trimethyl-2-(2-buten-1-ylidene)-cyclohexane.

4. A composition consisting essentially of about 15% cis/trans-1,4-epoxy-1,3,3-trimethyl-2-(2-buten-1-ylidene)-cyclohexane and about 85% trans/trans-1,4-epoxy-1,3,3-trimethyl-2-(2-buten-1-ylidene)-cyclohexane.

* * * * *